United States Patent [19]

Miyagi

[11] Patent Number: 4,706,657
[45] Date of Patent: Nov. 17, 1987

[54] LIGHT QUANTITY ADJUSTER FOR ENDOSCOPE APPARATUS

[75] Inventor: Kunihiko Miyagi, Tokyo, Japan

[73] Assignee: Kabushiki Kaisha Machida Seisakusho, Tokyo, Japan

[21] Appl. No.: 883,107

[22] Filed: Jul. 8, 1986

[30] Foreign Application Priority Data

Jul. 19, 1985 [JP] Japan .............................. 60-109612[U]

[51] Int. Cl.$^4$ ................................................ A61B 1/06
[52] U.S. Cl. ......................................................... 128/6
[58] Field of Search ............................ 128/6, 4, 3, 5, 7

[56] References Cited

U.S. PATENT DOCUMENTS 4,444,462  4/1984  Ono et al. ............................ 128/6 X

Primary Examiner—William H. Grieb
Attorney, Agent, or Firm—Kane, Dalsimer, Kane, Sullivan and Kurucz

[57] ABSTRACT

In an endoscope apparatus, an illuminating light is supplied from a light source unit to an end of an optical transmission system of an endoscope, and the optical transmission system has the other end allowing the illuminating light to be irradiated from an illuminating window located at a predetermined position of an inserting portion of the endoscope. The illuminating light has a luminous flux which is imaginarily divided into at least two regions including central and peripheral regions. An adjusting device is provided for adjusting a light quantity supplied to the one end of the optical transmission system through the central region of the luminous flux and a light quantity supplied to the one end of the optical transmission system through the peripheral region of the luminous flux, independently of each other.

20 Claims, 32 Drawing Figures

LIGHT QUANTITY ADJUSTER FOR ENDOSCOPE APPARATUS

BACKGROUND OF THE INVENTION

The present invention relates to an endoscope apparatus and, more particularly, to a device for adjusting a light quantity of an illuminating light for an endoscope depending upon used manners of the endoscope.

Figure 1:
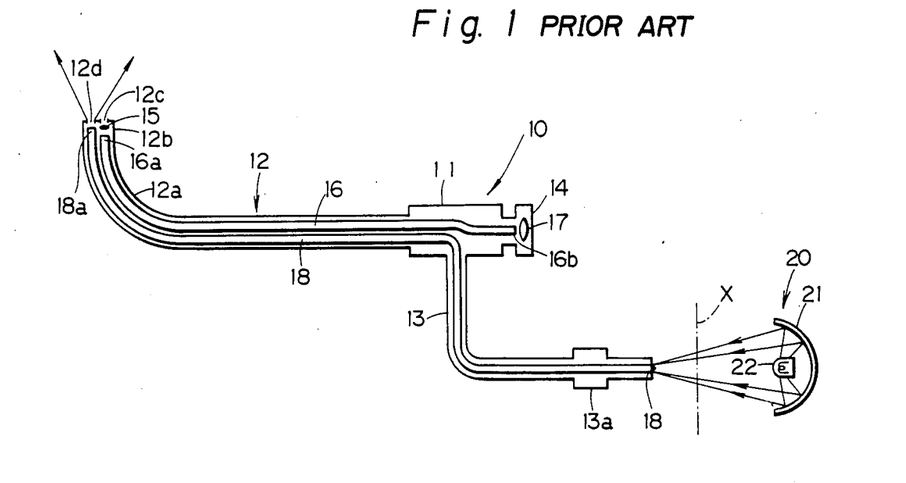
FIG. 1 is a diagrammatic view showing a conventional endoscope apparatus.

FIG. 1 shows a conventional endoscope apparatus which comrpises a usual endoscope 10 and a light source unit 20 for supplying an illuminating light to the endoscope 10. The endoscope 10 comprises an operating portion 11, an inserting portion 12 extending from the operating portion 11, a light guide cable 13 extending from the operating portion 11, and an ocular portion 14 provided at an end of the operating portion 11. The inserting portion 12 is flexible and is adapted to be inserted into a body cavity. The inserting portion 12 is comprised of a bendable section 12a adjacent a distal end of the inserting portion 12, and a hard or rigid tip component 12b at an end of the bendable section 12a adjacent the distal end of the inserting portion 12. The bendable section 12a has a curvature thereof which is controlled through a cable extending through the inserting portion 12 by a remote-control at the operating portion 11. The light guide cable 13 is provided at a distal end thereof with a plug 13a. The tip component 12b is provided in an end face thereof with a viewing window 12c and an illuminating window 12d. An optical fiber bundle 16 has one end 16a thereof which is optically connected to the viewing window 12c through an objective optical system 15. The optical fiber bundle 16 extends through the inserting portion 12 and the operating portion 11 and has the other end 16b optically connected to an ocular optical system 17 of the ocular portion 14. An optical transmission system, i.e., optical fiber bundle 18 has one end 18a thereof which is optically connected to the illuminating window 12d. The optical fiber bundle 18 extends through the inserting portion 12, the operating portion 11 and the light guide cable 13 and has the other end 18b which reaches a tip end of the plug 13a.

The light source unit 20 comprises a concave mirror 21 and a lamp 22 disposed at a center of the concave mirror 21.

A light from the lamp 22 is reflected from the concave mirror 21, and the reflected light is supplied to the other end 18b of the optical fiber bundle 18 while a luminous flux of the reflected light is gradually restricted. The light supplied to the other end 18b of the optical fiber bundle 18 passes through the bundle 18 and is irradiated into the body cavity from the illuminating window 12d. Thus, an interior of the body cavity is illuminated. An image of the illuminated interior of the body cavity is viewed through the viewing window 12c, objective optical system 15, optical fiber bundle 16 and ocular optical system 17.

Figure 3:
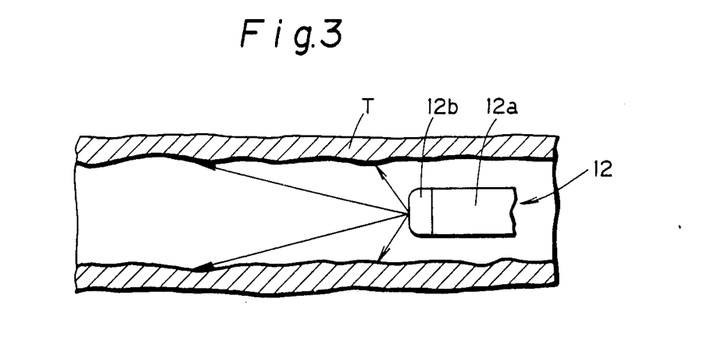
FIG. 3 is a cross-sectional view showing a used manner of an endoscope.
Figure 4:
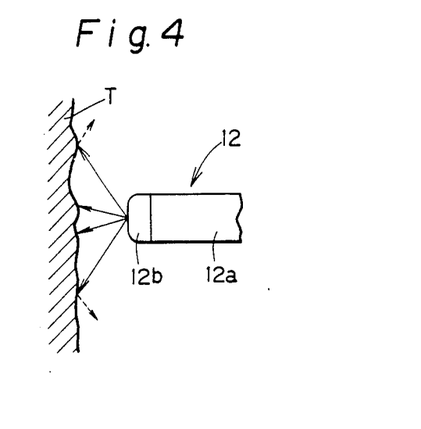
FIG. 4 is a view similar to FIG. 3, but showing another used manner of the endoscope.
Figure 5:
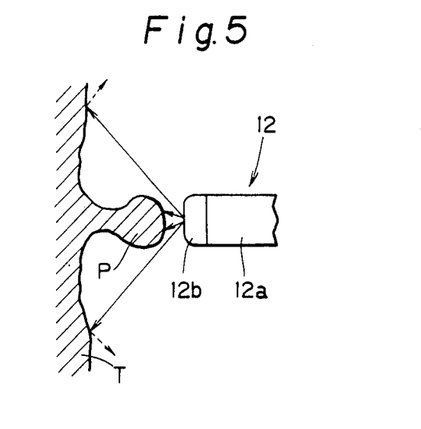
FIG. 5 is a view similar to FIG. 3, but showing still another used manner of the endoscope.

When the inserting portion 12 of the endoscope 10 is inserted into the body cavity such as, for example, an alimentary canal, a brightness of an image obtained at the ocular portion 14 varies depending upon conditions under which the endoscope 10 is disposed or positioned. For example, as shown in FIG. 3, when the endoscope 10 is disposed such that a field of view thereof is directed substantially longitudinally of the alimentary canal T, a proportion or rate of a light quantity of the light reflected and returned to the viewing window 12c of the inserting portion 12, with respect to the illuminating light having a constant light quantity is low, because a distance from the viewing window 12c to a wall surface of the alimentary canal T is long and an angle of the illuminating light with respect to the wall surface is small. By contrast, when, as shown in FIG. 4, the endoscope 10 views the alimentary canal T in such a manner that the illuminating window 12d and the viewing window 12c of the inserting portion 12 face to the wall surface of the alimentary canal T, and when, as shown in FIG. 5, the endoscope 10 views a convex morbid part such as a polyp P, a proportion of a light quantity of the light reflected and returned to the viewing window 12c, with respect to the illuminating light having a constant light quantity is high, because a distance from the illuminating window 12d to the wall surface of the alimentary canal T or the surface of the polyp P is short and an angle of the illuminating light with respect to such surface is great, in particular, the light in a central region of a luminous flux of the illuminating light from the illuminating window 12d is applied to such surface substantially perpendicularly. Accordingly, when the illuminating light is utilized which has a constant light quantity, the brightness of the image obtained at the ocular portion 14 varies as a whole depending upon the used manners of the endoscope 10.

It is necessary for the image at the ocular portion 14 to have an adequate or suitable brightness. The image which is too bright or dark would hinder photographing and observation of the image. For this purpose, a light quantity adjusting device is disposed in position indicated by the dot-and-dash line X in FIG. 1 between the light source unit 10 and the tip end of the plug 13a, i.e., the other end 18b of the optical fiber bundle 18, for adjusting the light quantity of the illuminating light supplied from the light source unit 20 to the other end 18b of the optical fiber bundle 18.

Figure 6:
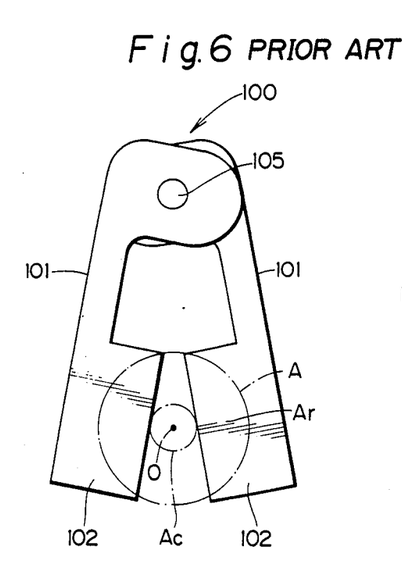
FIG. 6 is a front elevational view of a conventional light quantity adjusting device.
Figure 7:
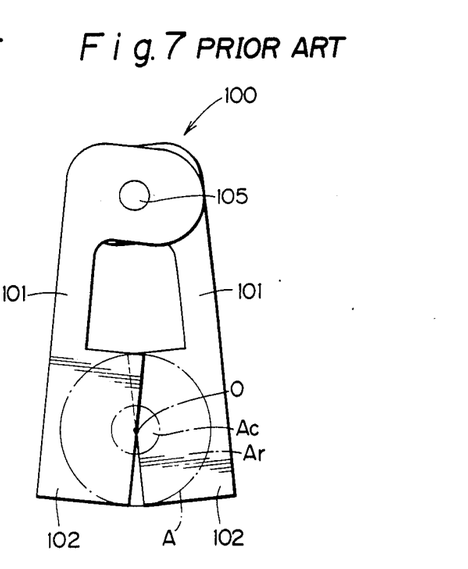
FIG. 7 is a view similar to FIG. 6, but showing a luminous flux more restricted by the adjusting device than the condition shown in FIG. 6.

As shown in FIGS. 6 and 7, a conventional light quantity adjusting device 100 as is disclosed in Japanese Patent Publication No. 47-44644 and Japanese Utility Model Publication No. 51-16286, comprises a pair of elongated shield members 101 and 101 which have their respective upper ends mounted on a common pivot shaft 105 for angularly movement therearound. Recutangular shield elements 102 and 102 are integrally connected to lower ends of the respective shield members 101 and 101, respectively, and cooperate with each other to variably shield, the luminous flux A of the illuminating light from the light source unit 20.

When the endoscope 10 is utilized under the condition shown in FIG. 3, the shield elements 102 and 102 are moved away from each other to enlarge a space therebetween, i.e., to fully open the luminous flux A, for example, to thereby increase the light quantity of the illuminating light supplied to the other end 18b of the optical fiber bundle 18. When the endoscope 10 is utilized under the conditions shown in FIGS. 4 and 5, the shield elements 102 and 102 are moved toward each other to reduce the space therebetween so as to bring the shield elements 102 and 102 to a restricted condition shown in FIG. 6, for example, to thereby decrease the light quantity of the illuminating light. In this manner, the brightness of the image at the ocular portion 14 is adjusted.

Figure 2:
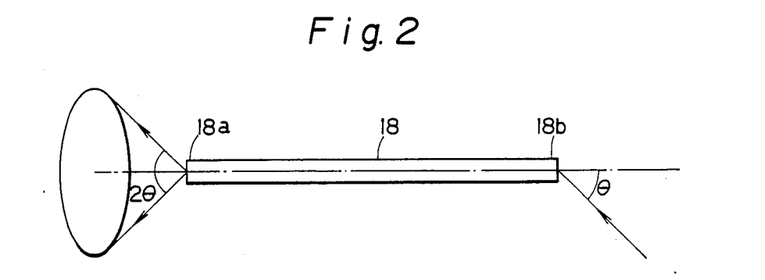
FIG. 2 illustrates the principle of transmission of an illuminating light by means of an optical fiber bundle.

In considering the above-described prior art and the present invention to be described later, it will be important to understand the transmission principle of illuminating light as shown in FIG. 2. Specifically, the light having an incidence angle $\theta$ supplied to the other end 18b of the optical fiber bundle 18 from the lamp 22 passes through the optical fiber bundle 18 and is irradiated into the body cavity from the one end 18a of the bundle 18 through the illuminating window 12d, but the irradiated light is in the form of a cone having a solid angle $2\theta$. Accordingly, as shown in FIG. 6 and 7, assuming that the luminous flux A is imaginarily divided in cross-section at the position X in FIG. 1 into a central region Ac including an optical axis 0 of the luminous flux A and the vicinity thereof and having a small incidence angle $\theta$, and a peripheral region Ar surrounding the central region Ac and having a large incidence angle $\theta$, when a portion of the peripheral region Ar is shielded by means of the above-described shield elements 102 and 102, the light quantity of a peripheral region of the illuminating light irradiated into the body cavity is decreased, but the light quantity of a central region of the illuminating light is not decreased. Conversely, when a portion of the central region Ac is shielded, the light quantity of only the central region of the illuminating light irradiated into the body cavity is decreased.

In addition, it is normal or usual that the central region of the illuminating light is higher in light quantity than the peripheral region thereof, because of the light diffusion characteristic of the optical fiber bundle.

It is possible for the above-described conventional light quantity adjusting device 100 to adjust the entire brightness of the image obtained at the ocular portion 14. However, no sufficient consideration has been made to a distribution of the brightness of the image. Hereunder, detailed description will be made to each of the used manners of the endoscope.

When the endoscope is disposed under the condition shown in FIG. 3, a deep portion of the alimentary canal T is imaged on a central region of the image obtained at the ocular portion 14, and the wall surface of the canal T adjacent the distal end of the inserting portion 12 is imaged on a peripheral region of the image. The wall surface adjacent the distal end of the inserting portion 12 is closer to the illuminating window 12d than the deep portion and, therefore, a proportion or rate of the light quantity returned from the wall surface to the viewing window 12c with respect to the constant light quantity irradiated from the illuminating window 12c is high. Accordingly, if the light is uniformly distributed, the peripheral region of the image would be too bright, and the central region of the image would be too dark. In practice, however, since the central region is higher in light quantity than the peripheral region due to the light diffusion characeristic of the optical fiber bundle, the brightness of the image obtained at the ocular portion 14 is uniformized as a whole, and substantially no problem would occur.

When the endoscope is disposed under the condition shown in FIG. 4 or 5, a major portion of the irradiated light in the central region of the field of view is reflected and returned to the viewing window 12c, because the distance from the viewing window to the wall surface or the polyp P is short and the angle of the irradiated light is approximately right angles. In the peripheral region of the field of view, however, only a portion of the irradiated light is returned to the viewing window 12c, because the distance from the illuminating window 12b to the wall surface is long and the angle of irradiated light is small as compared with that in the central region so that a major portion of the irradiated light is reflected as shown by the broken lines. For these reasons, in combination with the light diffusion characteristic of the optical fiber bundle 18, the central region of the image obtained at the ocular portion 14 becomes too bright as compared with the peripheral region of the image. In view of this, if the above-described adjusting device 100 is restricted as shown, for example, in FIG. 6, the central region Ac of the luminous flux A is not entirely shield, but only a portion of the peripheral region Ar is shield. Accordingly, although the entire light quantity supplied to the other end 18b of the optical fiber bundle 18 is reduced, the brightness of the central region of the image obtained at the ocular portion 14 is maintained unchanged and the brightness of the peripheral region of the image is reduced. This would further promote the ununiformity in brightness. Moreover, as the luminous flux is further restricted from the condition shown in FIG. 6, the central region Ac is shielded, but the peripheral region Ar is shielded more than that. This would not make it possible to relieve the ununiformity of the brightness, but would result in an insufficiency of the entire brightness. FIG. 7 shows a condition under which the shield elements 102 and 102 reach the optical axis 0 of the luminous flux A. Under the restricted condition, the central and peripheral regions Ac and Ar are, for the first time, shielded at the same rate. Under the restricted condition or a further restricted condition, however, the illumination is impossible.

OBJECT AND SUMMARY OF THE INVENTION

An object of the present invention is to provide an endoscope apparatus which makes it possible to uniformize a brightness of an image to be viewed.

According to the present invention, there is provided an endoscope apparatus comprising:

light source means;

an endoscope including an inserting portion having window means located at a predetermined position of said inserting portion, and optical means for transmitting an illuminating light from the light source means to the window means, the optical means having one end thereof supplied with the illuminating light from the light source means and the other end allowing the illuminating light to be irradiated from the window means;

the illuminating light from the light source means having a luminous flux imaginarily divided in cross-section into at least two regions including central and peripheral regions; and means for adjusting a light quantity of the illuminating light supplied to the one end of the optical means through the central region of the luminous flux and a light quantity of the illuminating light supplied to the one end of the optical means through the peripheral region of the luminous flux, independently of each other.

DETAILED DESCRIPTION

Various embodiments of the invention will be described in detail with reference to FIGS. 8 through 29 of the drawings, in which FIGS. 8 through 29, like reference numerals and characters are used to designate like or similar parts or components shown in FIGS. 1 through 7, and the description of such similar parts and components will therefore be omitted to avoid repetition and for simplification.

Figure 8:
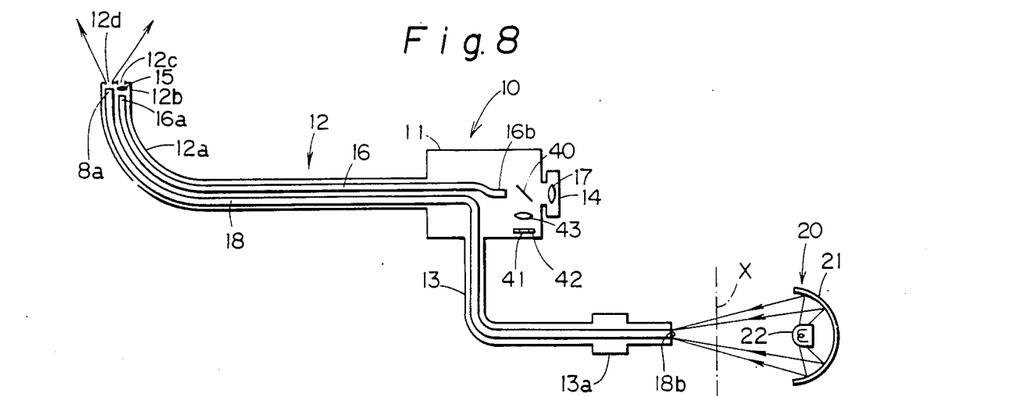
FIG. 8 is a view similar to FIG. 1, but showing an endoscope apparatus in accordance with an embodiment of the present invention.
Figure 9:
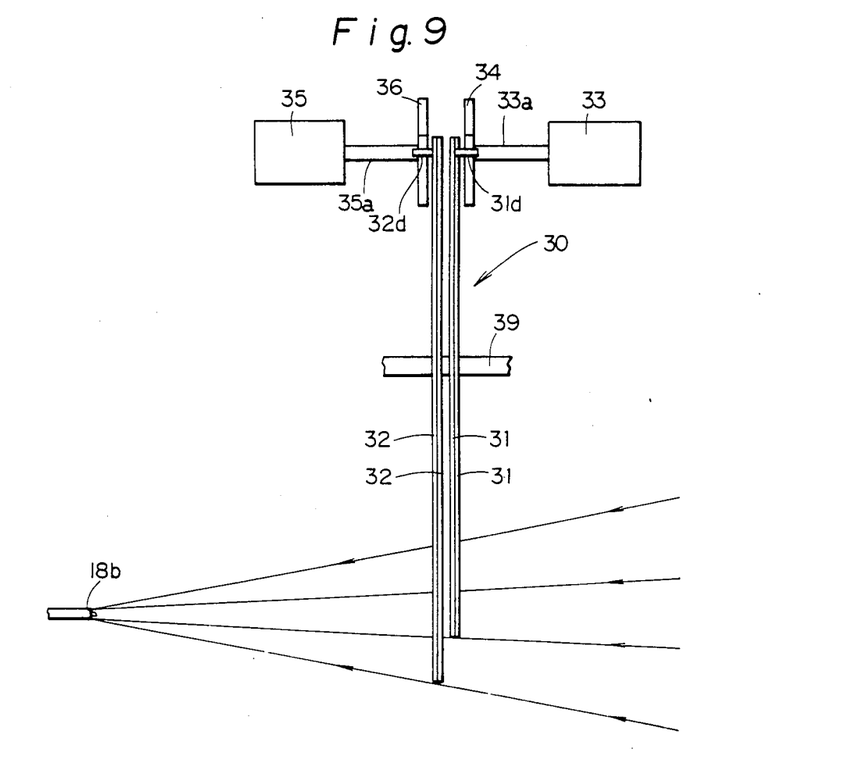
FIG. 9 is a side elevational view of a light quantity adjusting device incorporated in the apparatus shown in FIG. 8.

FIG. 8 shows as endoscope apparatus in accordance with an embodiment of the invention, which comprises a light quantity adjusting device 30 shown in FIG. 9 and located in position X between the endoscope 10 and the light source unit 20. The adjusting device 30 comprises a first pair of shielding members 31 and 31 and a second pair of shielding members 32 and 32, with the first and second pairs being located close to each other as shown in FIG. 9.

Figure 11:
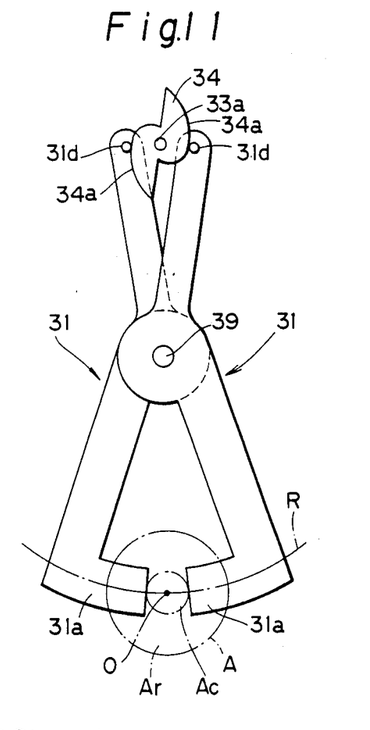
FIG. 11 is a front elevational view of another pair of shielding members of the adjusting device shown in FIG. 9.

As shown in FIG. 11, the first pair of shielding members 31 and 31 are symmetrical in configuration to each other. Each of the shielding members 31 and 31 is comprised of upper and lower legs integrally connected to each other at an angle and is mounted on a common pivot shaft 39 for angular movement therearound, at the connection between the upper and lower legs. A central shield element 31a in the form of an arc is integrally provided at a lower end of each of the shielding members 31, and a follower pin 31d is fixedly secured to an upper end of the shielding member 31. The shield elements 31a and 31a on the respective shielding members 31 and 31 extend toward each other along a locus inscribed by the lower ends of the respective shielding members 31 and 31 when they are angularly moved around the pivot shaft 39. When the shielding members 31 and 31 are angularly moved around the pivot shaft 39, the shield elements 31a and 31a are moved toward and away from each other along a locus of movement R between a shield position where the shield elements 31a and 31a are located close to each other to substantially fully shield the central region Ac and portions of the peripheral region Ar of the luminous flux A and an open position where the shield elements 31a and 31a are spaced from each other to substantially fully open the central region Ac and the portions of the peripheral region Ar.

Figure 10:
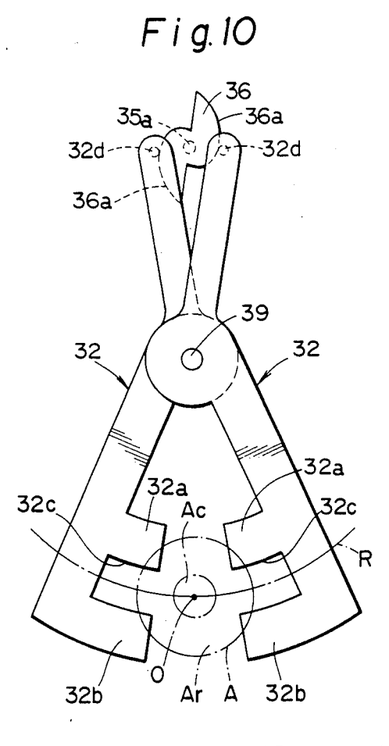
FIG. 10 is a front elevational view of a pair of shielding members of the adjusting device shown in FIG. 9.

As shown in FIG. 10, the second pair of shielding members 32 and 32 are symmetrical in configuration to each other, similarly to the first pair of shielding members 31 and 31. Each of the shielding members 32 is comprised of upper and lower legs integrally connected to each other at an angle, and is mounted on the above-described common pivot shaft 39 for angular movement therearound, at the connection between the upper and lower legs. A pair of peripheral shield elements 32a and 32b in the form of an arc are integrally provided at a lower end portion of each of the shielding members 32 and are spaced from each other along the lower leg thereof so as to define therebetween an arcuate space 32c substantially equal in width to a corresponding one of the central shield elements 31a and 31a of the respective shielding members 31 and 31. A follower pin 32d is fixedly secured to an upper end of each of the shielding members 32. The peripheral shield elements 32a and 32b on one of the pair of shielding members 32 and 32 and the peripheral shield elements 32a and 32b on the other shielding member 32 extend respectively toward each other along a locus of movement inscribed by the lower end portions of the respective shielding members 32 and 32 when they are angularly moved around the pivot shaft 39. When the shielding members 32 and 32 are angularly moved around the pivot shaft 39, the two pairs of peripheral shield elements 32a and 32b on the respective shielding members 32 and 32 are angularly moved toward and away from each other in parallel to the locus of movement R between a shield position where the two pairs of peripheral shield elements are located close to each other to substantially fully shield upper and lower portions of the peripheral region Ar and an open position where the two pairs of peripheral shield elements are spaced from each other to substantially fully open the upper and lower portions of the peripheral region Ar.

The first pair of shielding members 31 and 31 is actuated by a servomotor 33 (FIG. 9) to vary an opening angle therebetween. Specifically, a cam 34 is mounted on an end of an output shaft 33a of the servomotor 33 for rotation with the output shaft 33a. The shielding members 31 and 31 are biased by respective springs, not shown, in such a direction as to move the respective follower pins 31d and 31d toward each other to always bring them into contact with a cam surface 34a formed on a periphery of the cam 34. Angular movement of the cam 34 in the clockwise direction as viewed in FIG. 11 causes a distance from the output shaft 33a to the follower pins 31d and 31d to be progressively increased to angularly move the shield elements 31a and 31a on the respective shielding members 31 and 31 toward each other. Conversely, the angular movement of the cam 34 in the counterclockwise direction cause the shield elements 31a and 31a on the respective shielding members 31 and 31 to be moved away from each other.

The second pair of shielding members 32 and 32 are angularly moved by another servomotor 35 and a cam 36 mounted on an output shaft 35a of the servomotor 35 for rotation therewith, independently of the above-described first pair of shielding members 31 and 31, so that an opening angle between the shielding members 32 and 32 can be varied. Cam action by a cam surface 36a of the cam 36 and the follower pins 32d and 32d is similar to that of the cam 34 and the follower pins 31d and 31d associated with the shielding members 31 and 31, and will not be described to avoid duplication.

Figure 13:
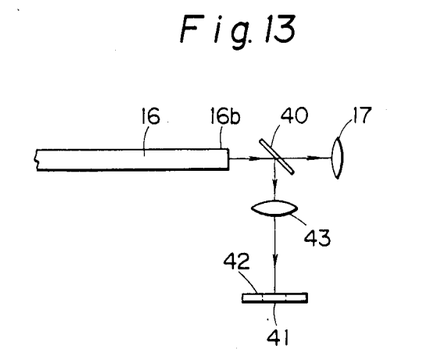
FIG. 13 is a fragmentary enlarged view showing a vicinity of an end, adjacent an ocular portion, of an optical fiber bundle forming an optical system for transmission of an image of the apparatus shown in FIG. 8.
Figure 14:
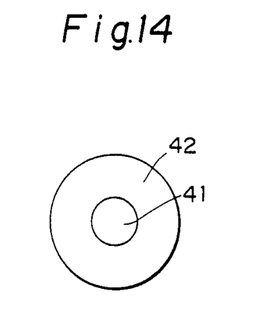
FIG. 14 is an enlarged top plan view of light quantity sensors shown in FIG. 13.
Figure 15:
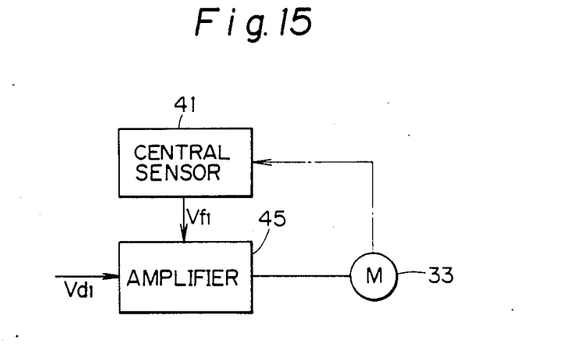
FIG. 15 is a block diagram showing a servo control circuit for the shielding members shown in FIG. 11.
Figure 16:
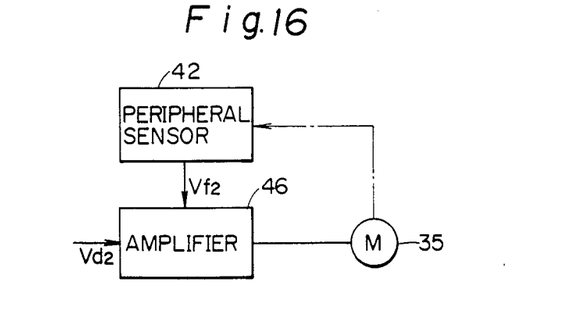
FIG. 16 is a block diagram showing a servo control circuit for the shield members shown in FIG. 10.

As shown in FIGS. 8 and 13, a translucent mirror 40 is disposed between the end 16b of the optical fiber bundle 16 and the ocular optical system 17, and serves to allow the light from the optical fiber bundle 16 to be transmitted through the mirror 40 to supply the light to the ocular optical system 17, and also serves to reflect the light to supply the same to central and peripheral sensors 41 and 42 through a convex lens 43. As shown in FIG. 14, the central sensor 41 is in the form of a disc, and the peripheral sensor 42 is in the form of an annulus. The central sensor 41 is disposed at a center of the peripheral sensor 42 in concentric relation thereto. Each of the sensors 41 and 42 is comprised of a plurality of light receiving diodes as a photoelectric transducer element, so that the central and peripheral sensors 41 and 42 and detect a total sum of light quantity of a central region of a luminous flux of the light from the end 16b of the optical fiber bundle 16 and a total sum of light quantity of a peripheral region of the luminous flux of the light from the end 16b, respectively, to generate detected voltage signals $Vf_1$ and $Vf_2$ representative of the respective light quantities. As shown in FIGS. 15 and 16, the signals $Vf_1$ and $Vf_2$ are sent respectively to amplifiers 45 and 46 which amplify a voltage difference between the voltage signal $Vf_1$ and a set voltage $Vd_1$ and a voltage difference between the voltage signal $Vf_2$ and a set voltage $Vd_2$, respectively, to generate actuating signals representative of the respective voltage differences. The servomotors 33 and 35 are operative respectively in response to the actuating signals from the amplifiers 45 and 46 to actuate the first and second pairs of shielding members 31 and 32.

With the construction as described above, the light from the lamp 22 is reflected by the concave mirror 21, and the reflected light is supplied to the other end 18b of the optical fiber bundle 18 while the luminous flux of the reflected light is gradually restricted. The light supplied to the other end 18b of the optical fiber bundle 18 passes through the bundle 18 and is irradiated into the body cavity from the illuminating window 12d so that the interior of the body cavity is illuminated. The image of the illuminated interior of the body cavity is viewed through the viewing window 12c, objective optical system 15, optical fiber bundle 16 and objective optical system 17. In addition, a portion of the light from the optical fiber bundle 16 is reflected by the translucent mirror 40 and is supplied to the central and peripheral sensors 41 and 42.

The central sensor 41 detects the light quantity of the central region of the image obtained at the ocular portion 14 and sends the detected voltage signal $Vf_1$ to the amplifier 45. The amplifier 45 amplifies the voltage difference between the signal $Vf_1$ and the set voltage $Vd_1$ corresponding to an optimum brightness, to generate the actuating signal which is supplied to the servomotor 33. When the detected voltage signal $Vf_1$ is higher than the set voltage $Vd_1$, i.e., when the brightness of the central region of the image obtained at the ocular portion 14 is too bright as compared with the optimum brightness, the servomotor 33 is rotated to rotate the cam 34 in the clockwise direction in FIG. 11, to angularly move the shield elements 31a and 31a of the respective shielding members 31 and 31 toward each other, to thereby partially shield the central region Ac of the luminous flux A.

The peripheral sensor 42 detects the light quantity of the peripheral region of the image obtained at the ocular portion 14 and sends the detected voltage signal $Vf_2$ to the amplifier 46. The amplifier 48 amplifies the voltage difference between the signal $Vf_2$ and the set voltage $Vd_2$ corresponding to an optimum brightness which is substantially the same level as the set brightness for the central region, to generate the actuating signal which is supplied to the servomotor 35. When the detected voltage signal $Vf_2$ is higher than the set voltage $Vd_2$, i.e., when the brightness of the peripheral region of the image obtained at the ocular portion 14 is too bright as compared with the optimum brightness, the servomotor 35 is rotated to rotate the cam 36 in the clockwise direction in FIG. 10, to angularly move the shield elements 32a and 32b of the respective shielding members 32 and 32 toward each other, to thereby partially shield the respective portions of the peripheral region Ar of the luminous flux A.

As described above, since the first and second pairs of shielding members 31 and 31 and 32 and 32 are controlled in their respective opening angles independently of each other, it is possible to substantially uniformize the distribution of brightness of the image obtained at the ocular portion 14 depending upon all of the used manners of the endoscope 10. For example, when the inserting portion 12 of the endoscope 10 is disposed as shown in FIG. 3, each of the first and second pairs of shielding members 31 and 31 and 32 and 32 are spaced from each other by a greater distance to fully open the luminous flux A. As a result, the brightness of the image obtained at the ocular portion 14 is substantially uniformized, as is the case of the above-described conventional apparatus.

If the peripheral region of the image obtained at the ocular portion 14 is rendered bright more than the central region thereof under the fully open condition as described above, only the second pair of shielding members 32 and 32 are restricted in the opening angle to partially shield portions of the peripheral region Ar of the luminous flux A. This causes the light quantity of the peripheral region Ar to be reduced, to thereby enable the brightness of the image to be uniformized.

When the inserting portion 12 of the endoscope 10 is disposed as shown in FIG. 4 or 5, the first pair of shielding members 31 and 31 are mainly restricted in the opening angle. As a result, only the central region Ac and the right and left portions of the peripheral region Ar are shielded and, in particular, the light quantity of the central region Ac can be reduced. Thus, it is possible to correct the ununiformity of the brightness distribution in the image at the ocular portion 14, which occurs due to the used manner shown in FIG. 4 or 5 and due to the light diffusion characteristic of the optical fiber bundle 18.

Figure 12:
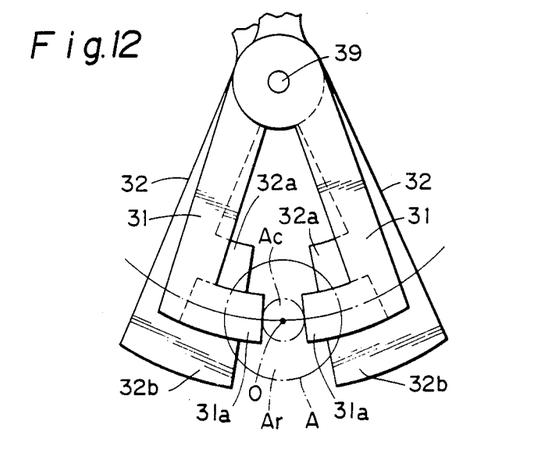
FIG. 12 is a fragmentary, front elevational view showing an assembly of the two pairs of shielding members shown respectively in FIGS. 10 and 11.
Figure 17:
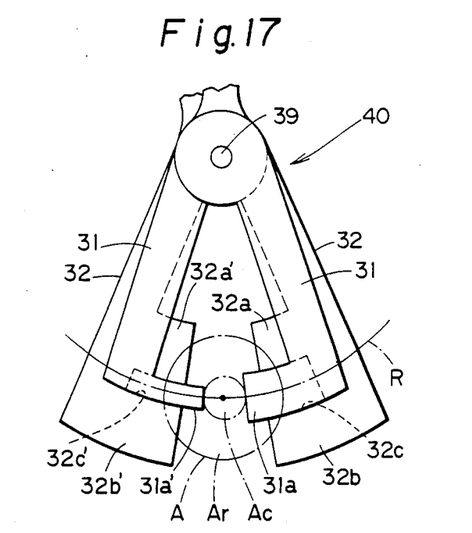
FIG. 17 is a view similar to FIG. 12, but showing a modification of the adjusting device.

FIG. 17 shows a modification of the light quantity adjusting device shown in FIGS. 10 through 12. A light quantity adjusting device 40 shown in FIG. 17 is similar to the adjusting device 30 shown in FIGS. 10 through 12, but is different therefrom in that the central shield element 31a' on one of the first pair of shielding members 31 has a width less than that of the central shield element 31a on the other shielding member 31, the peripheral shield elements 32a' and 32b' on one of the second pair of shielding members 32 have their respective widths respectively greater than those of the respective peripheral shield elements 32b and 32b on the other shielding member 32, and the space 32c' between the peripheral shield elements 32a' and 32b' is narrow correspondingly to the central shield element 31a'. With the construction, since right and left half regions of the luminous flux A are different in shielded area from each other, it is possible to releave a discontinuity of the light quantity which would otherwise occur at the boundary between the central and peripheral regions Ac and Ar.

Figure 18:
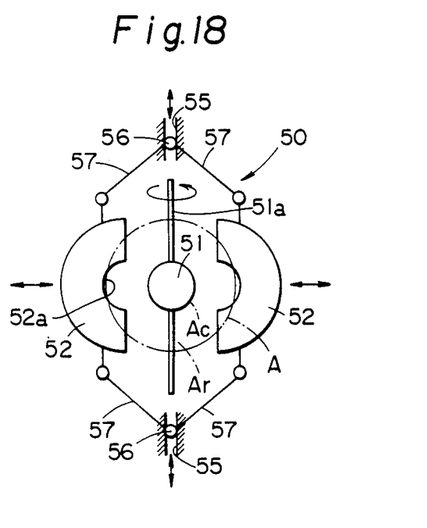
FIG. 18 is a diagramatic view showing another modification of the adjusting device.

A light quantity adjusting device shown in FIG. 18 in accordance with another modification comprises a central shield element 51 in the form of a disc disposed at the central region Ac of the luminous flux A, and a pair of peripheral shield elements 52 and 52 in the form of a semi-annulus. The central shield element 51 is supported by a shaft 51a extending perpendicularly to the optical axis of the luminous flux A and is actuated by the shaft 51a so as to be angularly moved around an axis of the shaft 51a between a shield position where a surface of the central shield element 51 extends substantially perpendicularly to the optical axis to substantially fully shield the central region Ac of the luminous flux A and an open position where the surface of the central shield element 51 extends substantially in parallel to the optical axis to substantially fully open the central region Ac. The pair of peripheral shield elements 52 and 52 are disposed at opposite sides of the central shield element 51 so as to be horizontally movable toward and away from each other. The peripheral shield elements 52 and 52 are connected to a pair of upper and lower sliders 56 and 56 through articulated links 57, and the sliders 56 and 56 are slidably received in vertically extending grooves 55 and 55, respectively, which are formed in respective mounts, not shown. Each of the peripheral shield elements 52 has an inner arcuate edge which has a radius of curvature substantially the same as a radius of the central shield element 51. The peripheral shield elements 52 and 52 are actuated by the sliders 56 and 56 so as to be moved toward and away from each other between a shield position where the peripheral shield elements 52 and 52 are located close to each other to substantially fully shield the peripheral region Ar of the luminous flux A and an open position where the peripheral shield elements 52 and 52 are spaced from each other to substantially fully open the peripheral region Ar of the luminous flux A. When the pair of sliders 56 and 56 are moved away from each other, the peripheral shield elements 52 and 52 are moved toward the shield position, and when the sliders 56 and 56 are moved toward each other, the peripheral shield elements 52 and 52 are moved toward the open position. The sliders 56 and 56 are actuated by servomotors in a manner similar to the described with reference to FIG. 15.

Figure 19:
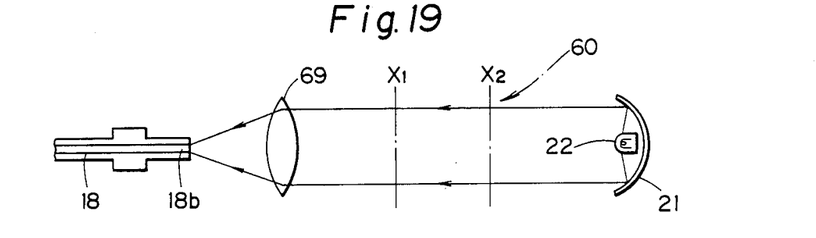
FIG. 19 is a diagramatic fragmentary view showing an endoscope apparatus in accordance with another embodiment of the present invention.
Figure 20:
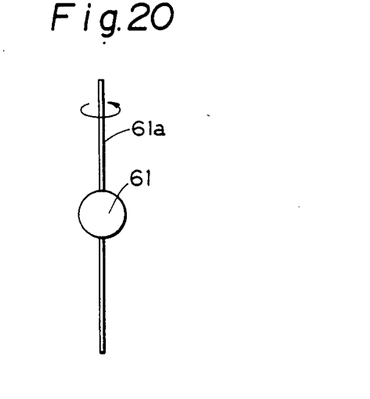
FIG. 20 is a front elevational view showing a central shield element of a light quantity adjusting device to be incorporated in the apparatus shown in FIG. 19.
Figure 21:
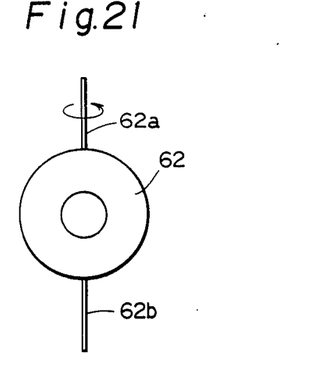
FIG. 21 is a front elevational view showing a peripheral shield element which cooperates with the central element shown in FIG. 20 to form the adjusting device.

FIG. 19 shows a portion of an endoscope apparatus in accordance with another embodiment of the invention, which is different from the apparatus shown in FIG. 8 only in that the light from the lamp 2 is reflected by the concave mirror 21 so as to form a parallel light ray, and the parallel light ray is condensed by a condenser 69 and is supplied to the other end 18b of the optical fiber bundle 18. A light quantity adjusting device utilized in the apparatus shown in FIG. 19 is shown in FIGS. 20 and 21 and comprises a central shield element 61 in the form of a disc and a peripheral shield element 62 in the form of an annulus. The central shield element 61 is disposed at a position $X_1$, and the peripheral shield element 62 is disposed at a position $X_2$ spaced from the position $X_1$ toward the mirror 21. The central shield element 61 is angularly moved by a shaft 61a around an axis thereof extending perpendicularly to an optical axis of the luminous flux of the light from the mirror 21, between a shield position where a surface of the central shield element 61 extends substantially perpendicularly to the optical axis to substantially fully shield the central region Ac of the luminous flux and an open position where the surface of the central shield element 61 extends substantially in parallel to the optical axis to substantially fully open the central region Ac. The peripheral shield element 62 is angularly moved by a pair of shaft sections 62a and 62b around a common axis thereof extending perpendicularly to the optical axis of the luminous flux, between a shield position where a surface of the peripheral shield element 62 extends substantially perpendicularly to the optical axis to substantially fully shield the peripheral region Ar of the luminous flux and an open position where the surface of the peripheral shield element 62 extends substantially in parallel to the optical axis to substantially fully open the peripheral region Ar.

Figure 22:
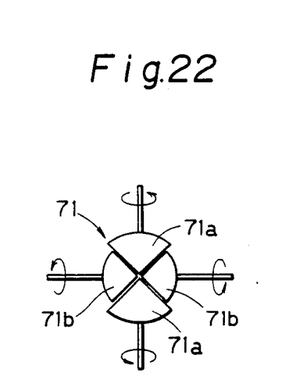
FIG. 22 is a view similar to FIG. 20, but showing a modification of the central shield element.
Figure 23:
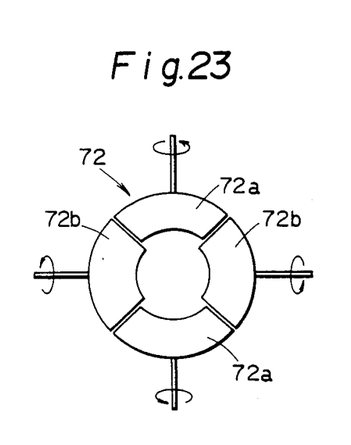
FIG. 23 is a view similar to FIG. 21, but showing a modification of the peripheral shield element.

FIGS. 22 and 23 show a modification of the light quantity adjusting device shown in FIGS. 20 and 21. Specifically, a central shield element 71 disposed at the position $X_1$ shown in FIG. 19 is comprised of first and second pairs of segments 71a and 71a and 71b and 71b, with each segment being in the form of a fan. The first pair of segments 71a and 71a are opposed to each other and have the same surface area, and the second pair of segments 71b and 71b are also opposed to each other and have the same surface area. However, the first and second pairs of segments 71a and 71a and 71b and 71b are different in total surface area from each other. The first and second pairs of segments 71a and 71b and 71b are angularly moved by their respective shafts in a manner similar to that described with reference to FIG. 20. A peripheral shield element 72 disposed at the position $X_2$ shown in FIG. 19 is comprised of first and second pairs of segments 72a an 72a and 72b and 72b, with each segment being in the form of an arc. The first pair of segments 72a and 72a are opposed to each other and have the same surface area, and the second pair of segments 72b and 72b are also opposed to each other and have the same surface area. However, the first and second pairs of segments 72a and 72a and 72b and 72b are different in total surface area from each other. Each of the first pair of segments 72a has an inner edge having the same radius of curvature as that of an outer edge of the corresponding segment 71a of the central shield element 71, and each of the second pair of segments 72b has an inner edge having the same radius of curvature as that of an outer edge of the corresponding segment 71b of the central shield element 71. The first and second pairs of segments 72a and 72a and 72b and 72b are angularly moved by their respective shafts in a manner similar to that described with reference to FIG. 21.

With the construction shown in FIGS. 22 and 23, right and left portions and upper and lower portions of the luminous flux A are different in shielded area from each other and, therefore, it is possible to relieve a discontinuity of the light quantity which would occur at the boundary between the central and peripheral regions Ac and Ar, so that it is possible to perform the smooth adjustment of light quantity.

The segments 71a and 71b have been described as having a different surface area, but may have the same surface area and, similarly, the segments 72a and 72b may have the same surface area. In addition, the segments 71a and 71b may be actuated independently of each other or may be actuated simultaneously so as to have the same angular position. Similarly, the segments 72a and 72b may be actuated independently of each other or may be simultaneously actuated so as to have the same angular position.

Additionally, only a half of the luminous flux may be variably shielded by a shielding member which comprises a central shield element and a peripheral shield element. In this case, the central and peripheral shield elements are controlled independently of each other.

Figure 24:
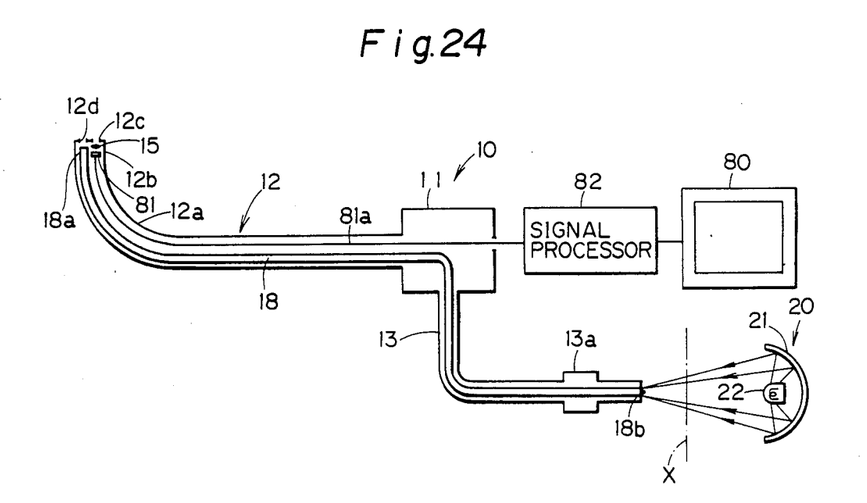
FIG. 24 is a view similar to FIG. 8, but showing an endoscope apparatus in accordance with still another embodiment of the present invention.
Figure 25A:
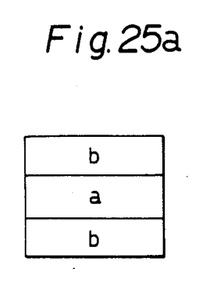
FIG. 25a and 25b show a manner to detect brightnesses of respective central and peripheral regions of an image to be projected on a screen of a television, with FIG. 25a diagrammatically showing the image imaginarily divided into three regions, and with FIG. 25b showing a wave form of a picture signal.
Figure 25B:
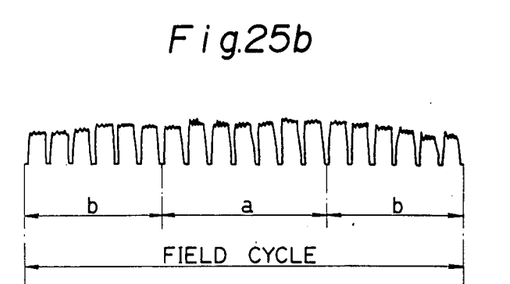
Figure 26A:
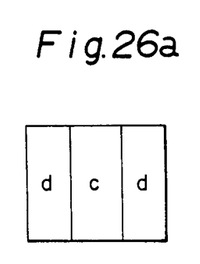
FIGS. 26a and 26b are views respectively similar to FIGS. 25a and 25b, but showing another detecting manner.
Figure 26B:
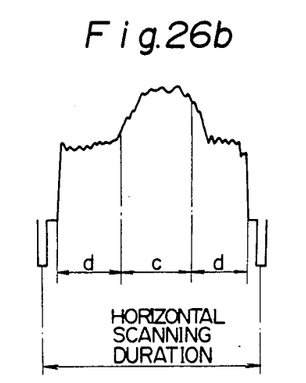
Figure 27A:
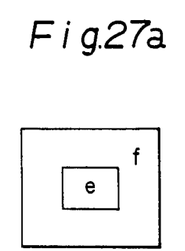
FIGS. 27a and 27b are views respectively similar to FIGS. 25a and 25b, but showing still another detecting manner.
Figure 27B:
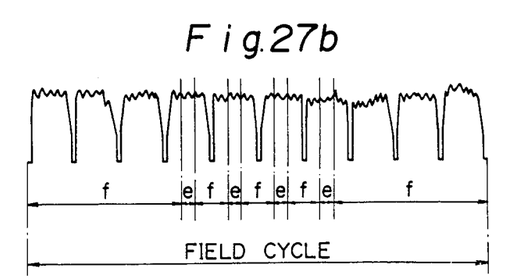

FIG. 24 shows an endoscope apparatus in accordance with another embodiment of the invention, which utilizes a solid state image pickup element or image sensor 81 in substitution for the optical fiber bundle 16 shown in FIG. 8. Specifically, the image sensor 81 is disposed adjacent the objective optical system 15 in the distal end 12b of the inserting portion 12 of the endoscope 10 and is connected by a lead wire 81a to a television 80 through a signal processor 82. An image of the interior of the body cavity, i.e., an image to be viewed is sensed by the image sensor 81 and is converted thereby to picture signals. The picture signals are supplied to the signal processor 82 where the picture signals are converted to television signals. The television 80 receives the television signals from the signal processor 82, and the image to be viewed is projected on a screen of the television 80. In this case, it is possible to detect the brightnesses of the respective central and peripheral regions of the image to be projected on the screen of the television 80, based on the television signals. There are three manners to detect the brightnesses. First one of the detecting manners is shown in FIGS. 25a and 25b, in which the image to be projected on the screen of the television 80 is imaginarily divided into three regions including a central region a and upper and lower regions b as shown in FIG. 25a. The brightnesses of respective regions are detected at the signal processor 82, based on integrated values of luminance levels of the television signals corresponding to the respective regions a and b in one field cycle as shown in FIG. 25b, to generate signals representative of the respective detected brightnesses. Central and peripheral shield elements for respectively shielding the central and peripheral regions of the luminous flux are controlled in response to the signals representative of the detected brightnesses, independently of each other, in a manner similar to that described above. FIGS. 26a and 26b show the second detecting manner in which the image to be projected on the screen of the television 80 is imaginarily divided into three regions including a central region c and right and left regions d as shown in FIG. 26a. As shown in FIG. 26b, the brightnesses of respective regions are detected at the signal processor 82, based on integrated values of luminance levels of the television signals corresponding to the respective regions c and d in one horizontal scanning duration, to generate signals representative of the respective detected brightnesses. Central and peripheral regions of the luminous flux are controlled in response to the signals representative of the respective detected brightnesses, independently of each other, in a manner similar to the described previously. The third detecting manner shown in FIGS. 27a and 27b is most ideal. The image to be projected on the screen of the television 80 is imaginarily divided into two regions including central and peripheral regions e and f as shown in FIG. 27a. As shown in FIG. 27b, the brightnesses of respective regions are detected at the signal processor 82, based on integrated values of luminance levels of the television signals corresponding to the respective regions e and f in one field cycle, to generate signals representative of the respective detected brightnesses. Central and peripheral regions of the luminous flux are controlled in response to the signals representative of the detected brightnesses, independently of each other.

Figure 28:
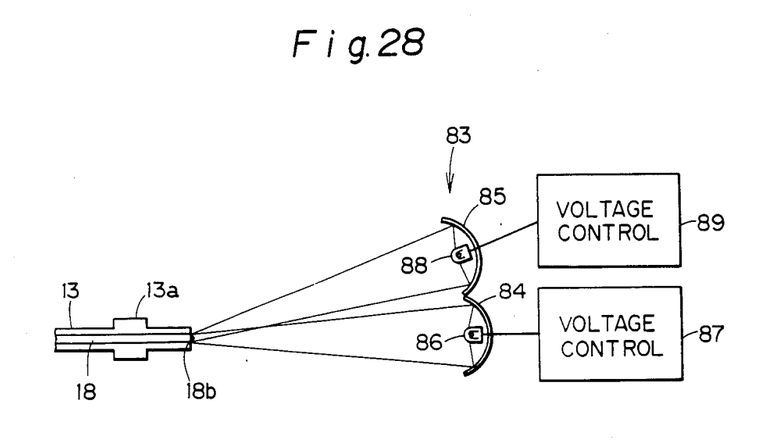
FIG. 28 is a diagrammatic fragmentary view showing an endoscope apparatus in accordance with still further embodiment of the present invention.

FIG. 28 shows an endoscope apparatus in accordance with still another embodiment of the invention, which does not comprise shield elements. A light source unit 83 shown in FIG. 28 comprises a first concave mirror 84 disposed in coaxial relation to the optical fiber bundle 18 and a second concave mirror 85 having a central axis thereof extending at an angle with respect to the longitudinal axis of the optical fiber bundle 18. A lamp 86 is associated with the first concave mirror 84 and is electrically connected to a voltage controller 87, and a lamp 88 is associated with the second concave mirror 85 and is electrically connected to a voltage controller 89 separate from the voltage controller 87. A light from the lamp 88 is reflected from the first concave mirror 84 and is supplied to the other end 18b of the optical fiber bundle 18 through a central region of an entire luminous flux from the light source unit 83, and a light from the lamp 88 is reflected from the second concave mirror 85 and is supplied to the other end 18b of the optical bundle 18 through a peripheral region of the entire luminous flux from the light source unit 83. The voltage controllers 87 and 89 are supplied with signals from a detector which may be any one of the detectors described with reference to FIGS. 13 and 14 and FIGS. 24 through 27, and are controlled in response to signals from the detector, independently of each other, to vary the light quantities supplied to the other end 18b of the optical fiber bundle 18 for the respective lamps 86 and 88.

Figure 29:
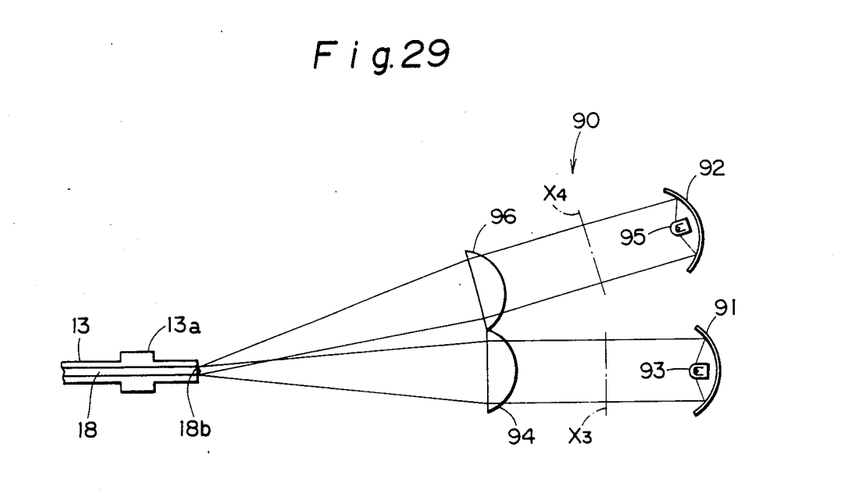
FIG. 29 is a view similar to FIG. 28, but showing an endoscope apparatus in accordance with another embodiment of the present invention.

FIG. 29 shows an endoscope apparatus in accordance with still further embodiment of the invention, which comprises a light source unit 90. The light source unit 90 includes a first concave mirror 91 disposed in coaxial relation to the optical fiber bundle 18 and a second concave mirror 92 having a central axis thereof extending at an angle with respect to the longitudinal axis of the optical fiber bundle 18. A lamp 93 is associated with the first concave mirror 91, and a light from the lamp 93 is reflected from the first concave mirror 91 so as to form a parallel light ray. The parallel light ray is condensed by a condenser 94 and is supplied to the other end of the optical fiber bundle 18 through a central region of an entire luminous flux from the light source unit 90. Similarly, light from a lamp 95 associated with the second concave mirror 92 is reflecterd from the second concave mirror 92, is condensed by a condenser 96, and is supplied to the other end 18b of the optical fiber bundle 18 through a periperal region of the entire luminous flux from the light source unit 90. A shield element, not shown, in the form of a disc similar to the shield element 61 shown in FIG. 20 or a pair of shield elements similar to those 102 and 102 shown in FIG. 6 is or are located at positions $X_3$ and $X_4$.

It should be appreciated that the central and peripheral shield elements may be controlled manually by actuating mechanisms independent of each other.

Although the invention has been described as having the luminous flux A which is divided into two regions including central and peripheral regions Ac and Ar, these regions are imaginary, and the luminous flux may be divided into three or more including a central region, a peripheral region and an intermediate region therebetween. In this case, shield elements for the respective regions are controlled independently of each other.

As described above, in the present invention, a luminous flux of an illuminating light is divided into a plurality of regions at least including central and peripheral regions, and light quantities supplied to an end of an optical transmission system respectively thorugh the regions are controlled or adjusted independently of each other. Thus, it is possible to uniformize the brightness distribution of an image to be viewed, to enable superior photographing and observation to be conducted.

What is claimed is:

1. An endoscope apparatus comprising:
   light source means;
   an endoscope including an inserting portion having window means located at a predetermined position of said inserting portion, and optical means for transmitting an illuminating light from said light source means to said window means, said optical means having one end thereof supplied with the illuminating light from said light soruce means and the other end allowing the illuminating light to be irradiated from said window means;
   the illuminating light from said light source means having a luminous flux imaginarily divided in cross-section into at least two regions including central and peripheral reions; and
   means for adjusting a light quantity of the illuminating light supplied to said one end of said optical means through said central region of said luminous flux and a light quantity of the illuminating light supplied to said one end of said optical means through said peripheral region of said luminous flux, independently of each other.

2. An endoscope apparatus as defined in claim 1, wherein said adjusting means is disposed between said light source means and said one end of said optical means and comprises first and second shielding means associated respectively with said central and peripheral regions of said luminous flux, said first and second shielding means being actuated independently of each other to variably shield said central and peripheral regions, respectively.

3. An endoscope apparatus as defined in claim 2, including:
   means for detecting a brightness of a central one of at least two regions into which an image to be viewed is imaginarily divided, to generate a first signal, and for detecting a brightness of the other region of said image to be viewed to generate a second signal; and
   means operative in response to said first and second signals from said detecting means for respectively actuating said first and second shielding means independently of each other so as to cause each of said first and second shielding means to vary a shielded area of a corresponding one of said central and peripheral regions of said luminous flux.

4. An endoscope apparatus as defined in claim 2, wherein said first shielding means comprises a pair of central shield elements movable toward and away from each other between a shield position where said central shield elements are located close to each other to substantially fully shield a portion of said luminous flux including at least said central region thereof and an open position where said central shield elements are spaced from each other to substantially fully open at least said central region of said luminous flux, and wherein said second shielding means comprises a first pair of peripheral shield elements spaced from each other with one of said central shield elements being disposed between said first pair of peripheral shield elements, and a second pair of peripheral shield elements spaced from each other with the other central shield element being disposed between said second pair of peripheral shield elements, said first and second pairs of peripheral shield elements being movable toward and away from each other between a shield position where said first and second pairs of peripheral shield elements are located close to each other to substantially fully shield the remaining portion of said luminous flux and an open position where said first and second pairs of peripheral shield elements are spaced from each other to substantially fully open the remaining portion of said luminous flux.

5. An endoscope apparatus as deifined in claim 4, wherein said central and peripheral shield elements are angularly movable around a common axis.

6. An endoscope apparatus as defined in claim 5, wherein each of said central and peripheral shield elements is in the form of an arc.

7. An endoscope apparatus as defined in claim 5, wherein one of said pair of central shield elements has a width different from that of the other central shield element, and said first pair of peripheral shield elements being spaced from each other by a distance different from that by which said second pair of peripheral shield elements are spaced from each other.

8. An endoscope apparatus as defined in claim 2, wherein said first shielding means comprises a central shield element angularly movable around an axis perpendicular to an optical axis of said luminous flux between a shield position where a surface of said central shield element extends substantially perpendicularly to said optical axis to substantially fully shield said central region of said luminous flux and an open position where said surface of said central shield element extends substantially in parallel to said optical axis to substantially fully open said central region of said luminous flux, and a pair of peripheral shield elements movable toward and away from each other between a shield position where said pair of peripheral shield elements are located close to each other to substantially fully shield said peripheral region of said luminous flux and an open position where said pair of peripheral shield elements are spaced from each other to substantially fully open said peripheral region of said luminous flux.

9. An endoscope apparatus as defined in claim 8, wherein said central shield element is in the form of a disc, and each of said peripheral shield elements is in the form of a semi-annulus.

10. An endoscope apparatus as defined in claim 2, wherein said first shielding means comprises a central shield element angularly movable around an axis perpendicular to an optical axis of said luminous flux between a shield position where a surface of said central shield element extends substantially perpendicularly to said optical axis to substantially fully shield said central region of said luminous flux and an open position where said surface of said central shield element extends substantially in parallel to said optical axis to substantially fully open said central region thereof, and a peripheral shield element angular movable around an axis perpendicular to said optical axis between a shield position where a surface of said peripheral shield element extends substantially perpendicularly to said optical axis to substantially fully shield said peripheral region of said luminous flux and an open position where said surface of said peripheral shield element extends substantially in parallel to said optical axis to substantially fully open said peripheral reigon of said luminous flux.

11. An endoscope apparatus as defined in claim 10, wherein said central shield element is in the form of a disc, and said peripheral shield element is in the form of an annulus.

12. An endoscope apparatus as defined in claim 10, wherein each of said central and peripheral shield elements is comprised of a plurality of segments.

13. An endoscope apparatus as defined in claim 12, wherein each of said central and peripheral shield elements is comprised of two pairs of segments with each pair of segments being disposed in opposed relation to each other, one of said two pairs of segments being different in total surface area from the other pair of segments.

14. An endoscope apparatus as defined in claim 13, wherein each of said segments of said central shield element is in the form of a fan, and each of said segments of said peripheral shield element is in the form of an arc.

15. An endoscope apparatus as defined in claim 3, wherein said endoscope includes image sensor means disposed in a distal end of said inserting portion for sensing said image to be viewed formed by said illuminating light irradiated from said window means and for converting said image to be viewed to picture signals, said detecting means generating said first and second signals based on said picture signals.

16. An endoscope apparatus as defined in claim 15, wherein said image to be viewed is imaginarily divided into three regions extending in parallel to each other, said detecting means detecting a brightness of a central one of said three regions to generate said first signal and detecting a brightness of the remaining two regions to generate said second signal.

17. An endoscope apparatus as defined in claim 15, wherein said image to be viewed is imaginarily divided into two regions including central and peripheral regions, said detecting means detecting a brightness of said central region of said image to be viewed to generate said first signal and detecting a brightness of said peripheral region of said image to be viewed to generate said second signal.

18. An endoscope apparatus as defined in claim 3, wherein said endoscope includes an occur optical system for viewing said image to be viewed, and wherein said image to be viewed is imaginarily divided into two regions including central and peripheral regions, said detecting means being associated with said occular optical system for detecting a brightness of said central region of said image to be viewed to generate said first signal and detecting a brightness of said periperal region of said image to be viewed to generate said second signal.

19. An endoscope apparatus as defined in claim 18, wherein said detecting means comprises central sensor means in the form of a disc for detecting the brightness of said central region of said image to be viewed to generate said first signal, and peripheral sensor means in the form of an annulus for detecting the brightness of said peripheral region of said image to be viewed to generate said second signal, said central sensor means being disposed at a center of said peripheral sensor means.

20. An endoscope apparatus as defined in claim 1, wherein said light source means comprises a first light source for supplying the illuminating light to said one end of said optical means through said central region of said luminous flux and a second light source for supplying the illumiating light to said one end of said optical means through said peripheral region of said luminous flux, and wherein said adjusting means controls the light quantities of the luminus fluxes supplied to said one end of said optical means from said first and second light sources independently of each other.

* * * * *